United States Patent
Paley et al.

[11] Patent Number: 5,358,504
[45] Date of Patent: Oct. 25, 1994

[54] FIXATION BRACE WITH FOCAL HINGE

[75] Inventors: Dror Paley, Baltimore; John E. Herzenberg, Owings Mills, both of Md.; Mark S. Gosney; James E. Orsak, both of Memphis, Tenn.

[73] Assignee: Smith & Nephew Richards, Inc., Memphis, Tenn.

[21] Appl. No.: 57,744

[22] Filed: May 5, 1993

[51] Int. Cl.5 .............................. A61F 5/04
[52] U.S. Cl. .................. 606/56; 606/105; 606/58
[58] Field of Search .................... 606/53–59, 606/86, 87, 102, 103, 105

[56] References Cited

U.S. PATENT DOCUMENTS

| | | |
|---|---|---|
| 3,976,061 | 8/1976 | Volkov et al. . |
| 3,977,397 | 8/1976 | Kalnberz et al. . |
| 4,033,340 | 7/1977 | Kalnberz . |
| 4,135,505 | 1/1979 | Day . |
| 4,365,624 | 12/1982 | Jaquet . |
| 4,488,542 | 12/1984 | Helland . |
| 4,535,763 | 8/1985 | Jaquet . |
| 4,620,533 | 11/1986 | Mears . |
| 4,624,249 | 11/1986 | Alvarez Cambras . |
| 4,628,922 | 12/1986 | Dewar . |
| 4,662,365 | 5/1987 | Gotzen et al. . |
| 4,747,400 | 5/1988 | Koeneman et al. . |
| 4,768,524 | 9/1988 | Hardy . |
| 4,784,125 | 11/1988 | Monticelli et al. . |
| 4,889,111 | 12/1989 | Ben-Dov . |
| 4,919,119 | 4/1990 | Jonsson et al. . |
| 5,021,054 | 6/1991 | Monfardini et al. . |
| 5,026,372 | 6/1991 | Sturtzkopf et al. ............... 606/54 |
| 5,041,112 | 8/1991 | Mingozzi et al. ............... 606/54 |
| 5,074,866 | 12/1991 | Sherman et al. ............... 606/56 |
| 5,122,140 | 6/1992 | Asche et al. ............... 606/55 |

Primary Examiner—Tamara L. Graysay
Attorney, Agent, or Firm—Pravel, Hewitt, Kimball & Krieger

[57] ABSTRACT

This invention relates to a device and method to externally fix bone fractures and bone deformities by moving an arc gear member, which is attached to a first bone segment, through an arc shaped path so as to place the first bone segment in the desired position relative to a second bone segment.

33 Claims, 11 Drawing Sheets

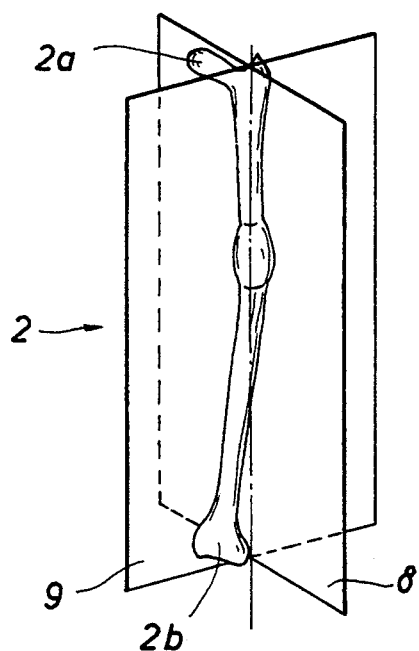
FIG.1
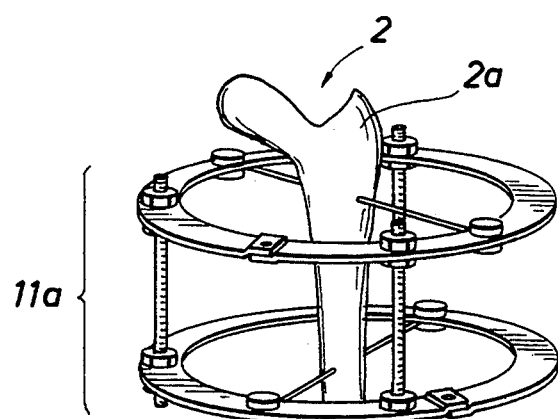
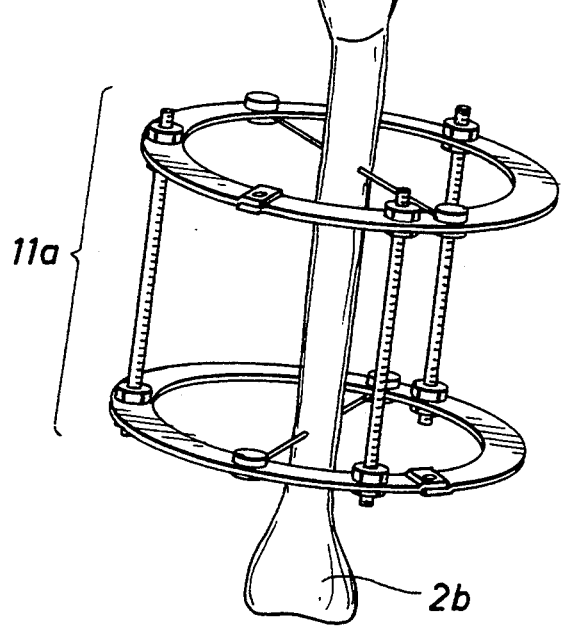
FIG.2

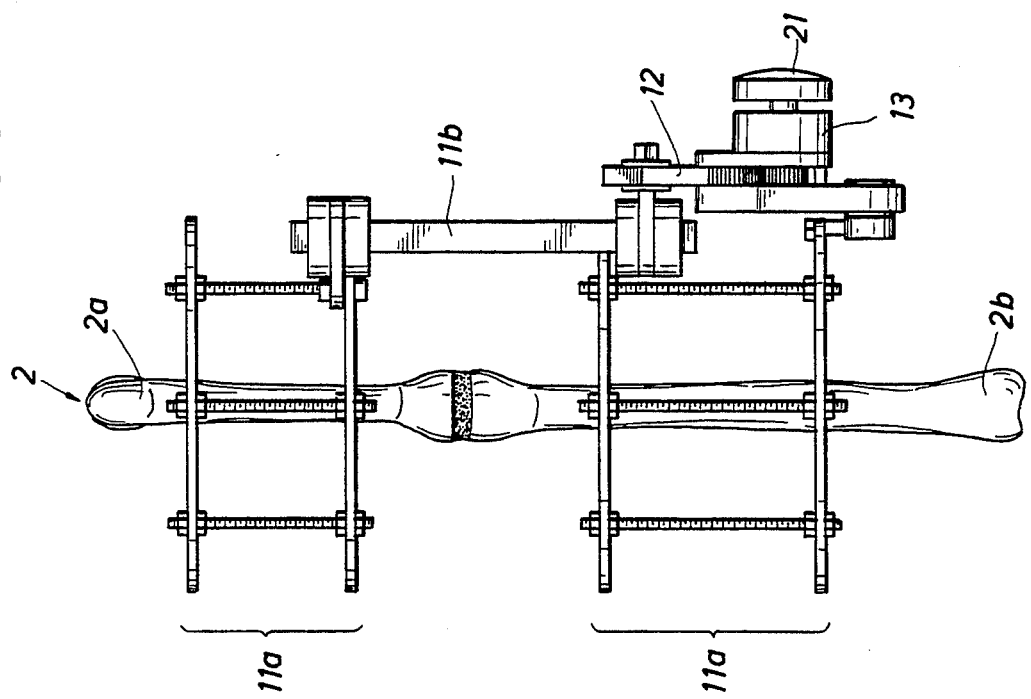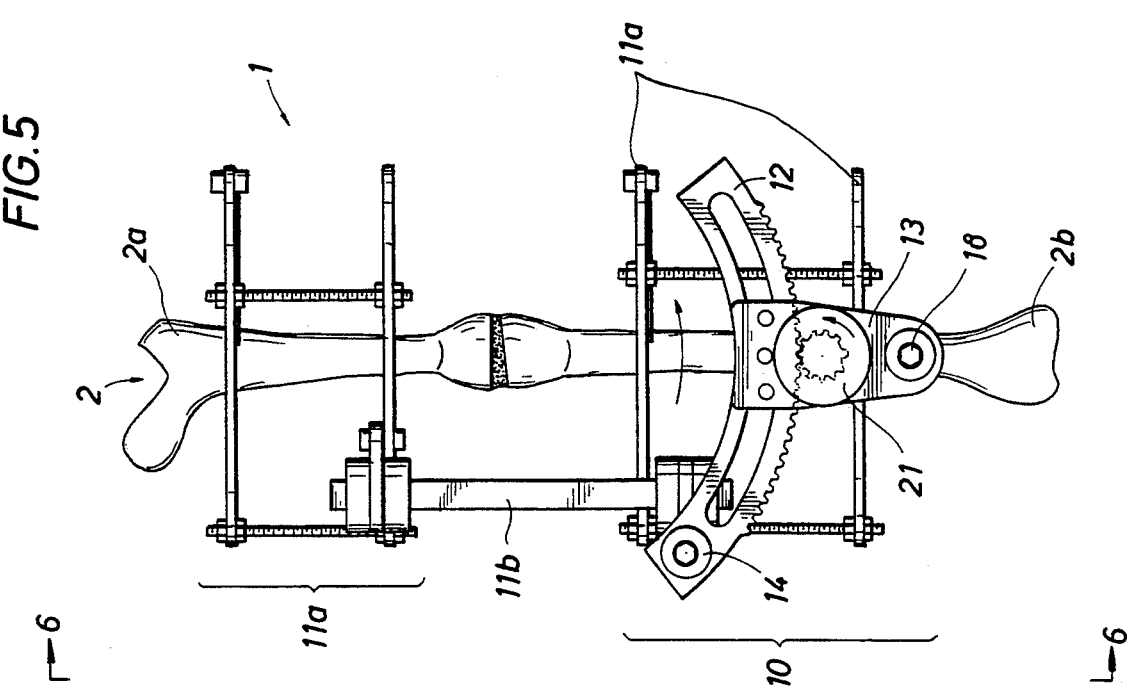

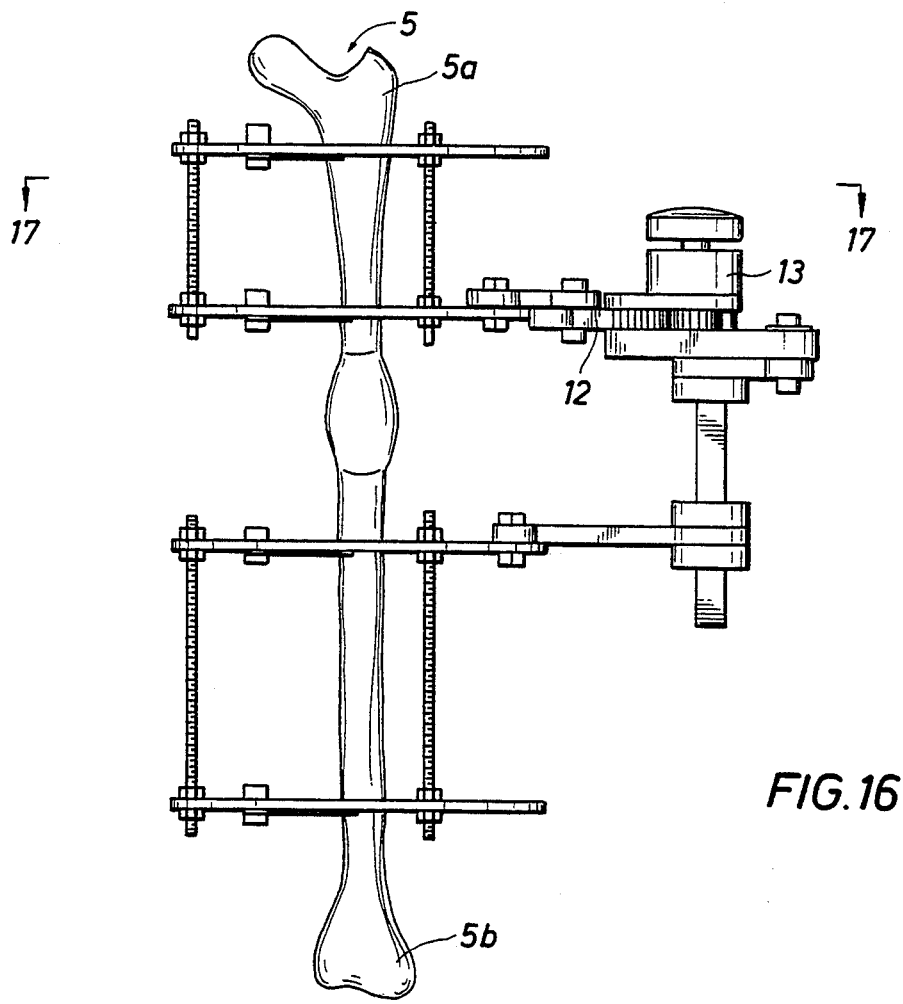
FIG. 16
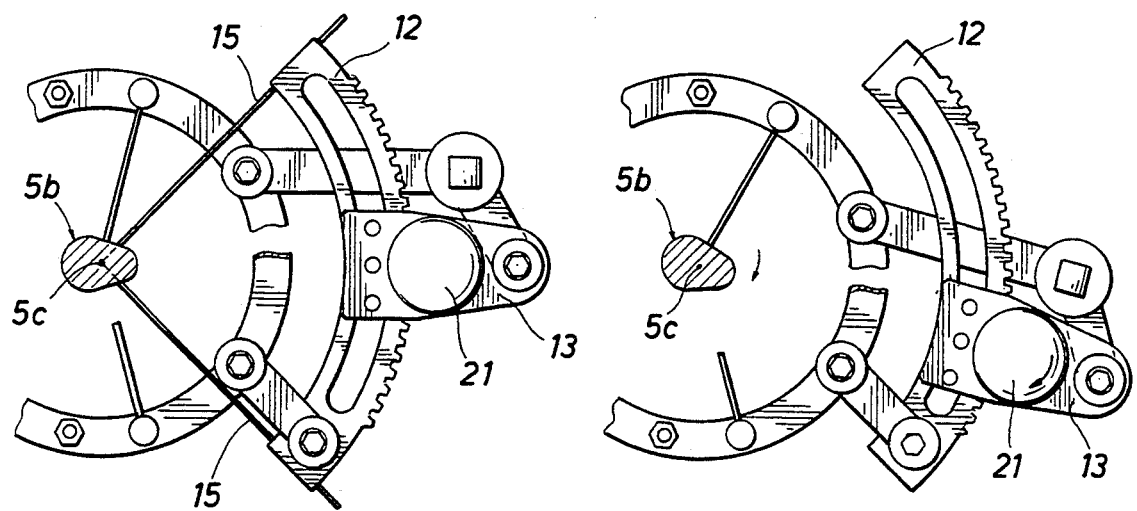
FIG. 17                    FIG. 18

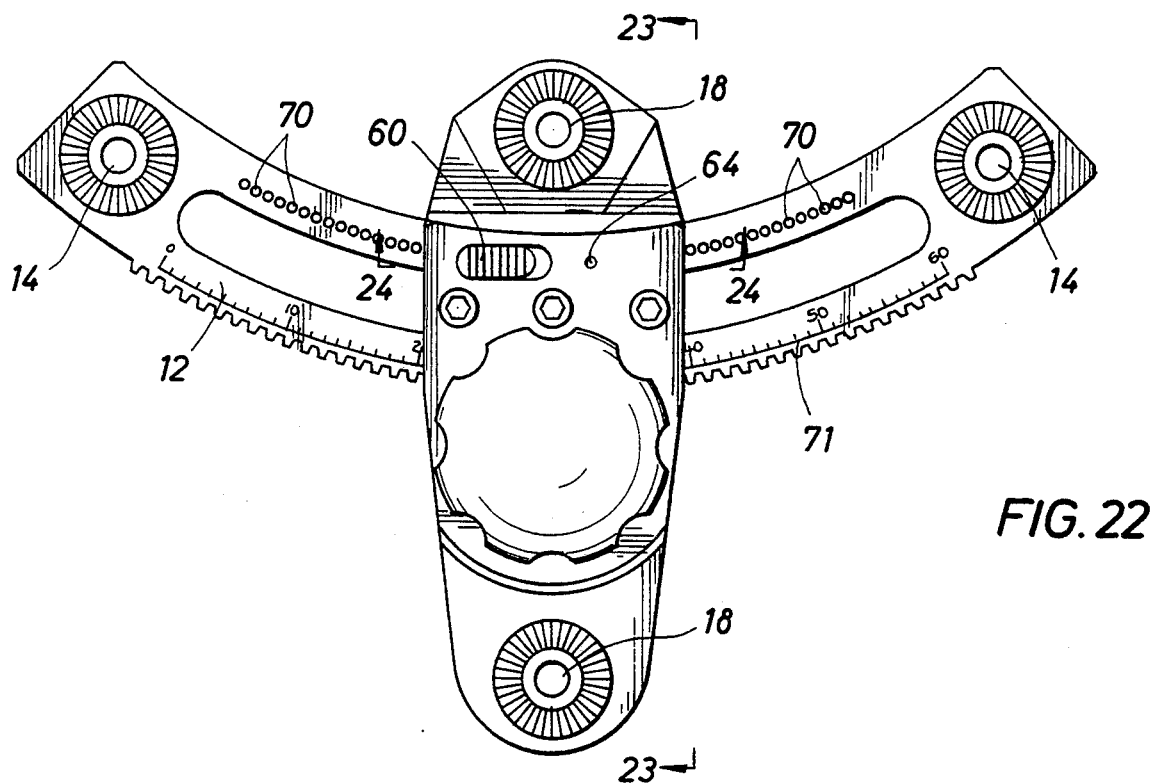
FIG. 22
FIG. 24
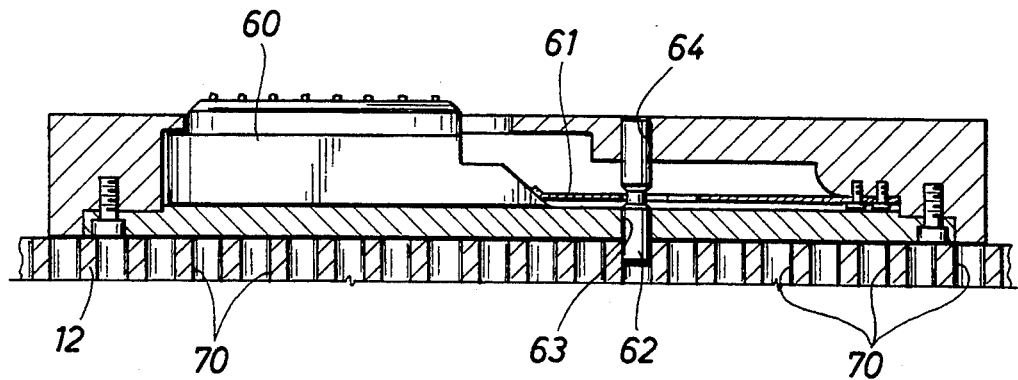
FIG. 25
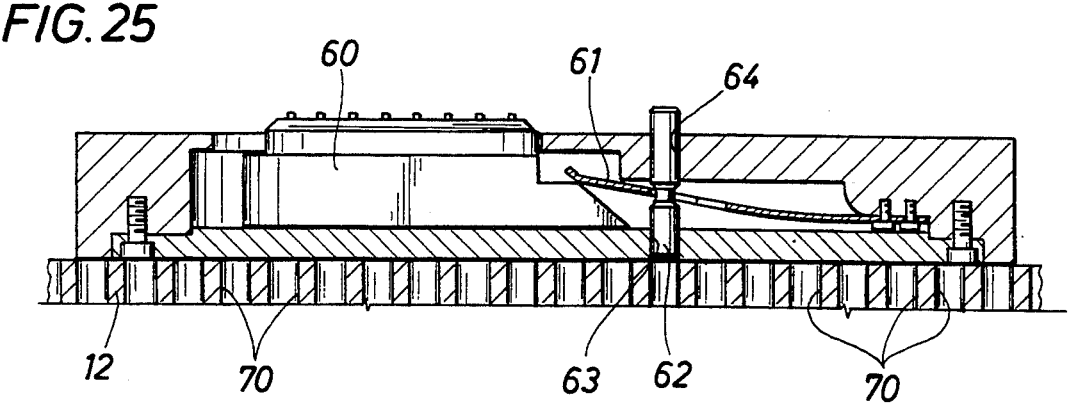

FIXATION BRACE WITH FOCAL HINGE

BACKGROUND OF THE INVENTION

1. Field of the Invention

This invention relates to a device and method for moving a first bone segment relative to a second bone segment to externally fix and stabilize bone fractures and to correct bone deformities. More particularly, this device provides an arc gear member which is attached to the first bone segment and a drive means which is attached to the second bone segment and which moves the first bone segment through an arc shaped path to place it in the desired position relative to the second bone segment.

2. Description of the Related Art

The present invention relates to a device for externally fixing and stabilizing bone fractures and correcting bone deformities. A number of devices for external corrections and setting of broken bones have been proposed with some models available on the market. With external fixation, generally, a first set of pins or wires are passed through the skin and soft tissues into the bone above the fracture or deformity and a second set of pins or wires are likewise inserted into the bone below the fracture or deformity. An external device is then connected to the sets of pins or wires to maintain the bone segments in the proper position. Also, there are a number of external devices including hinges, universal joints and ball joints which provide for moving the bone segments in relation to each other to achieve a more natural shape.

When alignment of bone segments is required, it is often desirable to move the bone segments slowly, over a period of several days to months, into the desired positions. This allows live bone cells, blood vessels, etc. located between the bone segments to continue to live and function, providing a stronger, more natural union upon complete correction. This alignment of bone segments is usually accompanied by either a corticotomy or osteotomy. A corticotomy consists of the removal of just the hard outer cortex of the bone while preserving periosteal and endosteal blood supplies. A corticotomy is generally sufficient for small to moderate bone movement. More significant bone movement may require an osteotomy wherein the bone is cut and removed to a greater extent. This method of slowly moving bone segments, over time, into the correct position is generally known as the Ilizarov method. When this slow movement is required, it is desirable that the motion be driven mechanically and that the drive mechanism be integral with the external brace such that medical personnel or the patient can easily and accurately move the bone segments.

Generally, when bone segments are required to be moved relative to each other, there are four types of movement: angular, rotational, translational-extension or compression, and translational-lateral.

There are a number of external devices which provide for at least some type of slow movement of bone segments relative to each other. Many of these devices provide for only one or two types of movements noted above. Other devices, such as, for example those shown in U.S. Pat. Nos. 4,033,340 and 4,488,542, provide for more complex movement.

There are several shortcomings associated with the known devices. First, many devices exist which provide for relatively simple movement of bone segments, e.g., translational-extension. Generally, these devices function satisfactorily for simple movement, however, many of the bone placement corrections require more complex movements than these devices can provide.

The devices which can provide more complex movement also suffer significant shortcomings. One such shortcoming is that these devices often require a "staged method" where one type of movement is made, then another type, in a stepwise, staged fashion. An example of the staged method would be first correcting the rotational movement, then correcting the translational movement, and finally correcting the angular movement. This is less desirable than the "one motion method" which simultaneously corrects for several or all types of motion. The staged method generally takes more time and therefore results in more discomfort, stress and trauma to the patient.

Another shortcoming with the known devices is that the placement of the device is often not very exact. Generally, more complex corrections are made by determining the plane of deformity and the required movement within that plane. Known devices do not provide an adequate means for aligning and positioning the device in the optimum position. Thus, often the optimum correction is not made or additional corrective steps are required.

Further, upon x-raying, the known devices can significantly block the view of the bone segments. Additionally, the known devices are often bulky and difficult to operate, thus adding error, weight and extra work to the application of the device.

Thus, there exists the need for a compact, non-obstructive external fixation device capable of moving two bone segments relative to each other through a vast range of complex corrective movements while allowing easy, accurate alignment and placement of the device.

SUMMARY OF THE INVENTION

The invention relates to an external fixation device which has an arc mechanism comprised of an arc gear member and drive means for moving the arc gear member. The arc gear member is generally arc shaped and has an attachment point which is connected to one bone segment which is desired to be moved relative to a second bone segment, the second bone segment being connected to the drive means. The arc mechanism moves the first bone segment, at the attachment point, through an arc shaped range of motion. As an aid in aligning and positioning the arc mechanism, the two ends of the arc gear member have spring clips which are designed to engage wires which represent the radii of the arc gear member. These wires aid in placing the device both in relation to the plane of deformity and the focal point of the arc shaped motion.

With the present invention, a surgeon presented with a bone fracture or deformity wherein external fixation is preferred will first take at least two x-rays at different angles to determine the plane of deformity and the focal point, by which, placement of the arc gear member in the plane of deformity (or parallel to the plane of deformity) and movement of the attachment point through an arc shaped range of motion will bring the bone segments into the desired alignment. Then, pins or wires are inserted into both bone segments, and external support braces are secured to each set of pins or wires. The attachment point of the arc gear member is secured to the support brace of that bone segment which is desired to be moved and the drive means is secured to the support brace of the stationary bone segment (or vise versa). In the placement and mounting of the arc mechanism, wires, representing the radii of the arc gear member, are used to ensure the arc mechanism is placed in a proper plane, with the focal point located as required.

The present invention provides an exterior fixation device which will correct bone placement via moving one bone segment through a vast range of corrective movements to bring it in alignment with a second stationary bone segment.

The present invention also provides a means for aligning and positioning an external fixation device to ensure that the optimum correction is made.

The present invention is also compact and designed to reduce blockage of x-rays, thus providing a better view of the bone segments and allowing quicker and easier application of the device.

BRIEF DESCRIPTION OF THE DRAWINGS

A better understanding of the invention can be obtained when the detailed description of exemplary embodiments set forth below is considered in conjunction with the attached drawings, in which:

FIG. 1 is a view of a deformed bone with intersecting medial-lateral and anterior-posterior planes.

FIG. 2 is a view of the deformed bone of FIG. 1 with support braces installed on the upper and lower bone segments.

FIG. 5 is a view of the deformed bone and device of FIG. 4 showing movement of the arc gear member.

FIG. 6 is a side view taken in the direction indicated by lines 6—6 of FIG. 5.

FIG. 16 is a view of the device attached to a deformed bone which requires rotational movement to correct the deformity.

FIG. 17 is a top view taken in the direction indicated by lines 17—17 of FIG. 16.

FIG. 18 is a view of the bone and device of FIG. 17 showing movement of the arc gear member to correct the deformity.

FIG. 22 shows an embodiment of the arc mechanism including additional features.

FIG. 24 is a sectional view of the arc mechanism taken in the direction indicated by lines 24—24 of FIG. 22.

FIG. 25 is a sectional view of the arc mechanism showing the thumb switch and pin in the disengaged position.

DETAILED DESCRIPTION OF EXEMPLARY EMBODIMENTS

Figure 4:
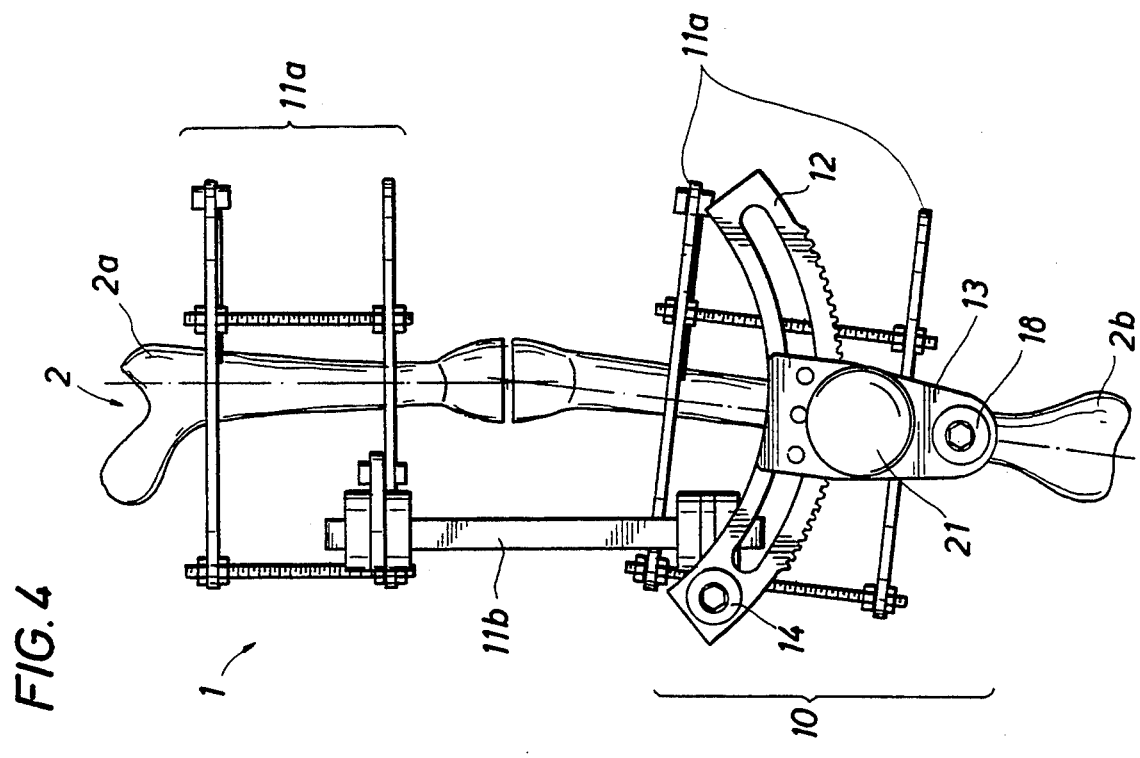
FIG. 4 is a view of the deformed bone of FIGS. 1, 2 and 3 showing the attachment of the arc mechanism onto the support braces.
Figure 3:
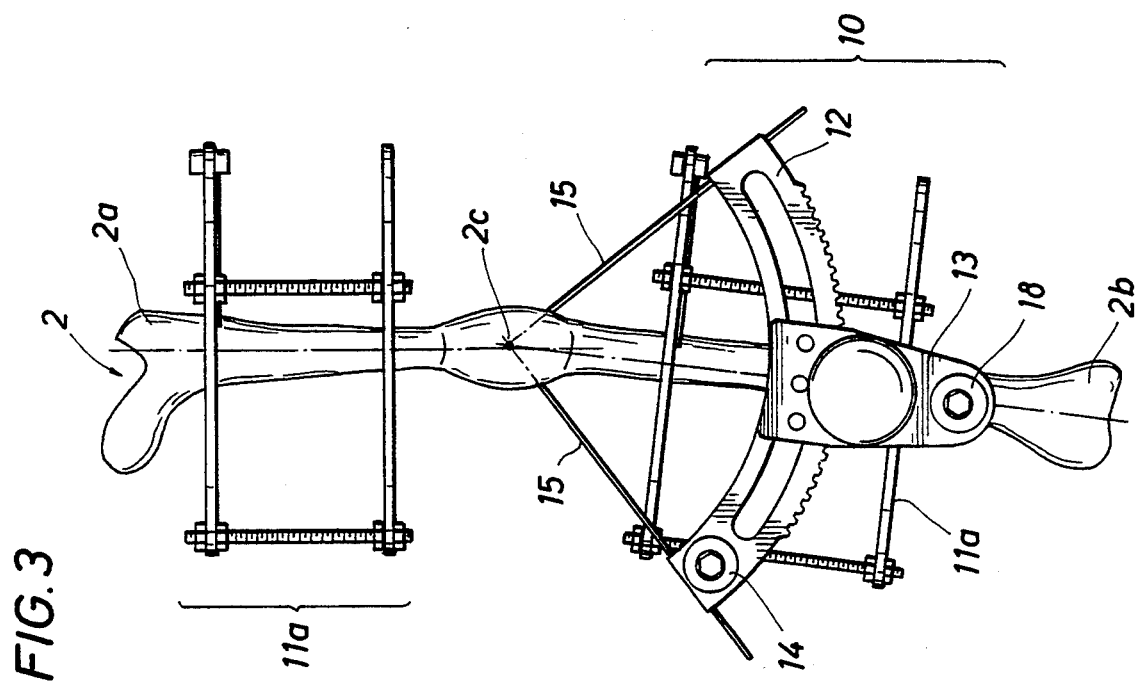
FIG. 3 is a view of the deformed bone of FIGS. 1 and 2 showing the use of alignment wires to align and position the device for correction of the bone deformity.
Figure 7:
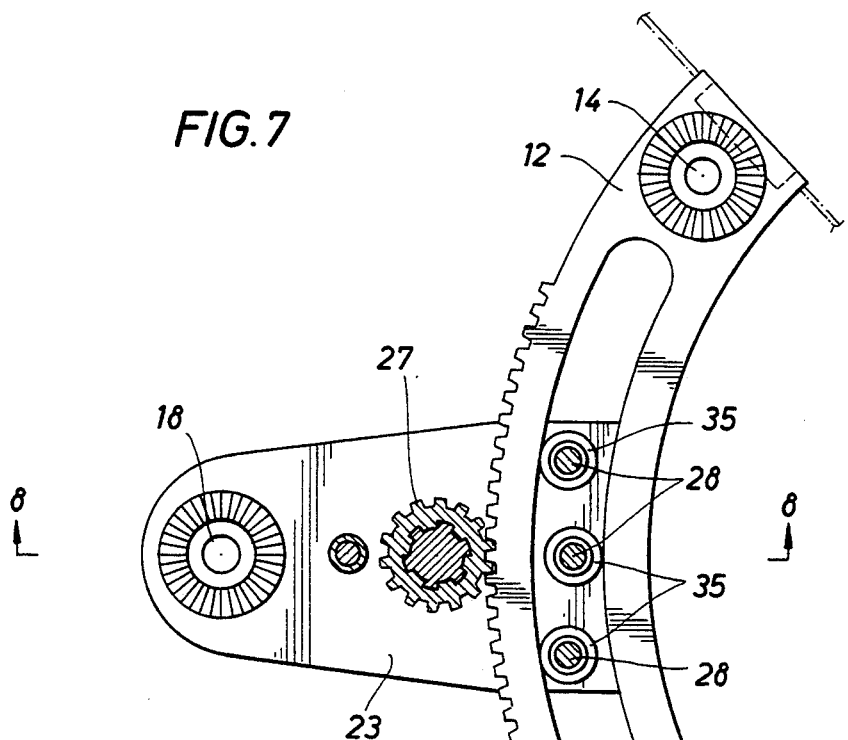
FIG. 7 is a sectional view of the arc mechanism showing the configuration of the arc gear member.
Figure 8:
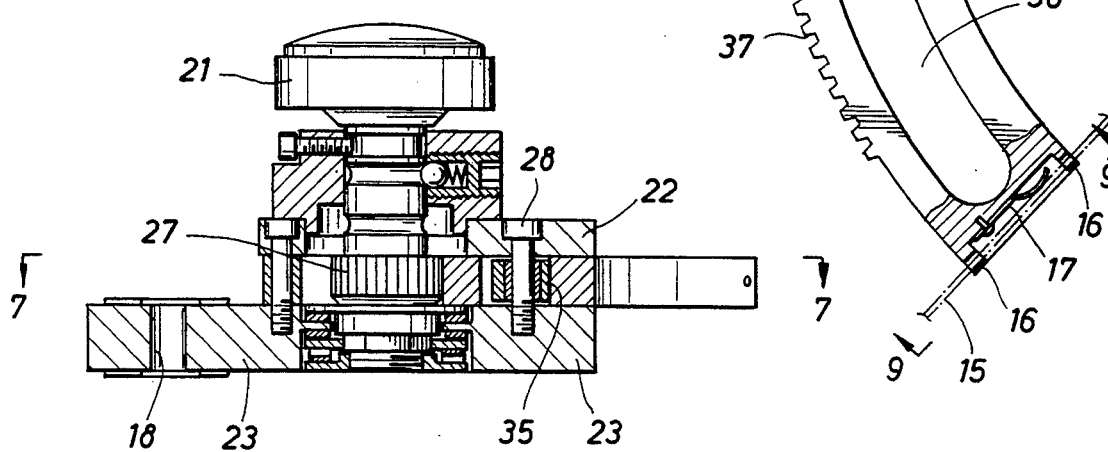
FIG. 8 is a sectional view of the arc mechanism taken in the direction indicated by lines 8—8 of FIG. 7.
Figure 9:
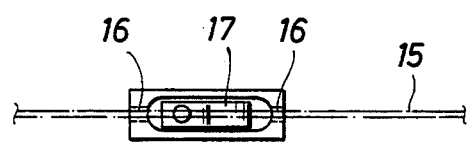
FIG. 9 is a side view taken in the direction indicated by lines 9—9 of FIG. 7.

FIGS. 3 and 4 shows one embodiment of a fixation brace with focal hinge device 1 which is formed of three major components: (1) an arc mechanism 10 having an arc gear member 12, a drive means 13 for moving the arc gear member 12, and means for aligning and positioning the arc mechanism 10 (alignment wires 15); (2) attachment means to secure the attachment point 14 of arc gear member 12 to a first bone segment (support braces 11a, 11b); and (3) attachment means to secure the drive means 13 to a second bone segment (support brace 11a).

In general, the device 1 is placed in use by first determining the "plane of deformity" and the "focal point" required to correct the bone deformity. Simply stated, the plane of deformity is that plane in which a rotative motion of one bone segment relative to the other bone segment will correct a given bone deformity. Also simply stated, the focal point is that point on the plane of deformity about which a rotational movement will correct a given bone deformity. The plane of deformity and focal point are determined using multiple x-rays of the deformed bone taken at different angles. Once the plane of deformity and focal point are determined, the arc mechanism 10 is positioned such arc gear member 12 is located in the plane of deformity (or a parallel plane) and the radii of the arc gear member 12 intersect at the focal point. Once the correct position of the arc mechanism 10 is determined, the arc gear member 12 is secured to one bone segment while the drive means 13 is secured to the second bone segment. The drive means 13 is manipulated to move the arc gear member 12 through an arc shaped range of motion such that the bone segments are brought into natural alignment relative to each other. The above steps may be performed in any sequence which will achieve the same overall result.

The device 1 and use of the device 1 may be more thoroughly understood with reference to the figures. FIGS. 1-6 show a bone 2 having a deformity as shown. To determine the plane of deformity and focal point, multiple X-rays are taken and analyzed. FIG. 1 shows the effective results of two X-rays; one a projection into the medial-lateral plane 8, and the other a projection into the anterior-posterior plane 9. In this instance, the surgeon would determine, as shown in FIG. 1, that the plane of deformity is located between the medial-lateral plane 8 and the anterior-posterior plane 9, i.e., the plane of deformity extends from the front-left to back-right. The focal point is that point in the plane of deformity about which a rotational movement of the bone segments relative to each other would bring the bone segments into the desired configuration. Here, the focal point 2c is located at approximately the center of the bulge in bone 2, as rotation about this point is required to bring the lower bone segment 2b into the correct position in relation to the upper bone segment 2a.

FIG. 2 shows the attachment of support braces 11a on the upper and lower bone segments 2a, 2b. As discussed below, the support braces 11a, 11b may be any of a variety of types.

FIG. 3 shows the aligning and positioning of the arc mechanism 10. Here, alignment wires 15, representing radii of arc gear member 12, aid in placing the arc mechanism 10 both in the plane of deformity and in positioning the arc gear member 12 such that its center of curvature is at the focal point 2c. As shown, the plane of deformity is the plane of the paper and the arc gear member 12, with alignment wires 15, is located in a plane parallel to the plane of deformity with alignment wires 15 pointing at a point directly above the focal point 2c and in the same plane as arc gear member 12.

FIG. 4 shows the attachment of the arc mechanism 10 to the upper and lower bone segments 2a, 2b. The arc gear member 12 is secured at attachment point 14 to the upper bone segment 2a via the upper support braces 11a, 11b. Drive means 13 is secured at drive attachment point 18 to the lower bone segment 2b via the lower support braces 11a (see FIG. 6).

In FIG. 4, the upper bone segment 2a would generally be stationary (proximal end of extremity), while the lower bone segment 2b would generally be moveable (distal end of extremity). Thus, since only one bone segment is generally moveable, it does not matter whether attachment point 14 and drive attachment point 18 are respectively secured to the upper or lower bone segments 2a, 2b. The same effect, i.e., arc shaped movement of the movable bone segment, will be achieved regardless of whether attachment point 14 (on arc gear member 12) is secured to the stationary bone segment or the moveable bone segment.

FIGS. 5 and 6 show the straightening of bone 2 which is achieved via turning knob 21 to move arc gear member 12, thus moving the lower bone segment 2b in the direction indicated. Slow movement of the arc gear member 12, over a period of several days to several months, will allow bone to grow and fill in the area between the two bone segments 2a, 2b.

The preferred embodiment of the arc mechanism 10 is shown in FIGS. 7-11. While arc gear member 12 may be of any arc shape, e.g. ellipse, oval or other curve, arc gear member 12 is preferably in the shape of a section of a circle which has a corresponding track of arc gear teeth 37. Most preferably, the section of arc member 12 is more than 10° and less than 90°. The arc member 12 has at least one attachment point 14 to secure it to a bone segment via support braces 11a, 11b. The two ends of arc member 12 are designed to receive and hold alignment wires 15. This is accomplished by passing the wires 15 through alignment holes 16 and compressing spring clip 17. The alignment wires 15 are designed so as to represent the radii of arc member 12. Arc member 12 and alignment wires 15 have a general planar shape, i.e., arc member 12 is flat and alignment wires 15 extend radially into the same plane.

Arc member 12 is designed to cooperate with and move via drive means 13. Arc member 12 is designed to slide between upper plate 22 and lower plate 23. Rollers 35, fastened with plate fastener 28 and extending between upper plate 22 and lower plate 23, fit within the arc shaped slot 36 of arc member 12 to prevent unwanted radial movement.

Drive means 13 is manipulated by turning knob 21. Knob 21 is connected, via pin 33, to both gear shaft 25 and spline gear 24. Gear shaft 25 extends axially beyond spline gear 24, this extended portion has shaft gear teeth 38 which engage clutch mechanism 40, which controls the amount of force required to turn knob 21.

Figure 10:
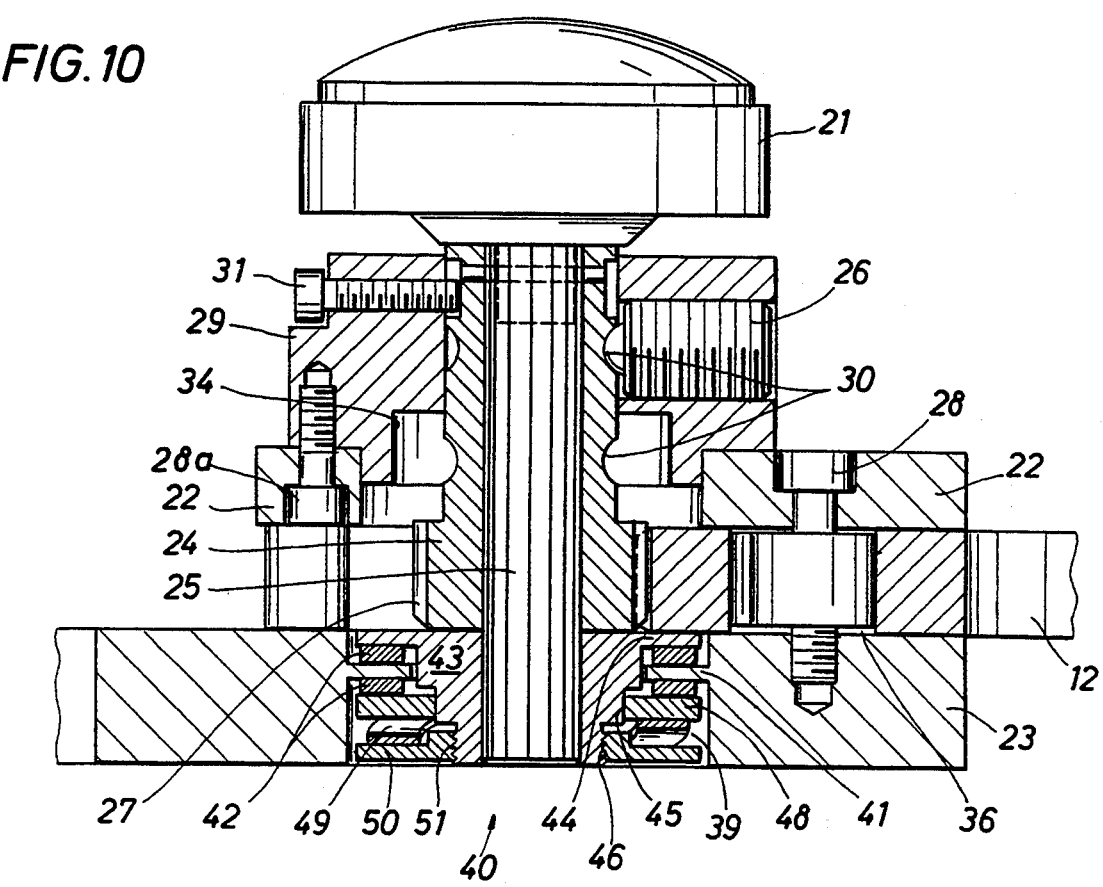
FIG. 10 is a sectional view of the arc mechanism showing the knob in the retracted position.
Figure 11:
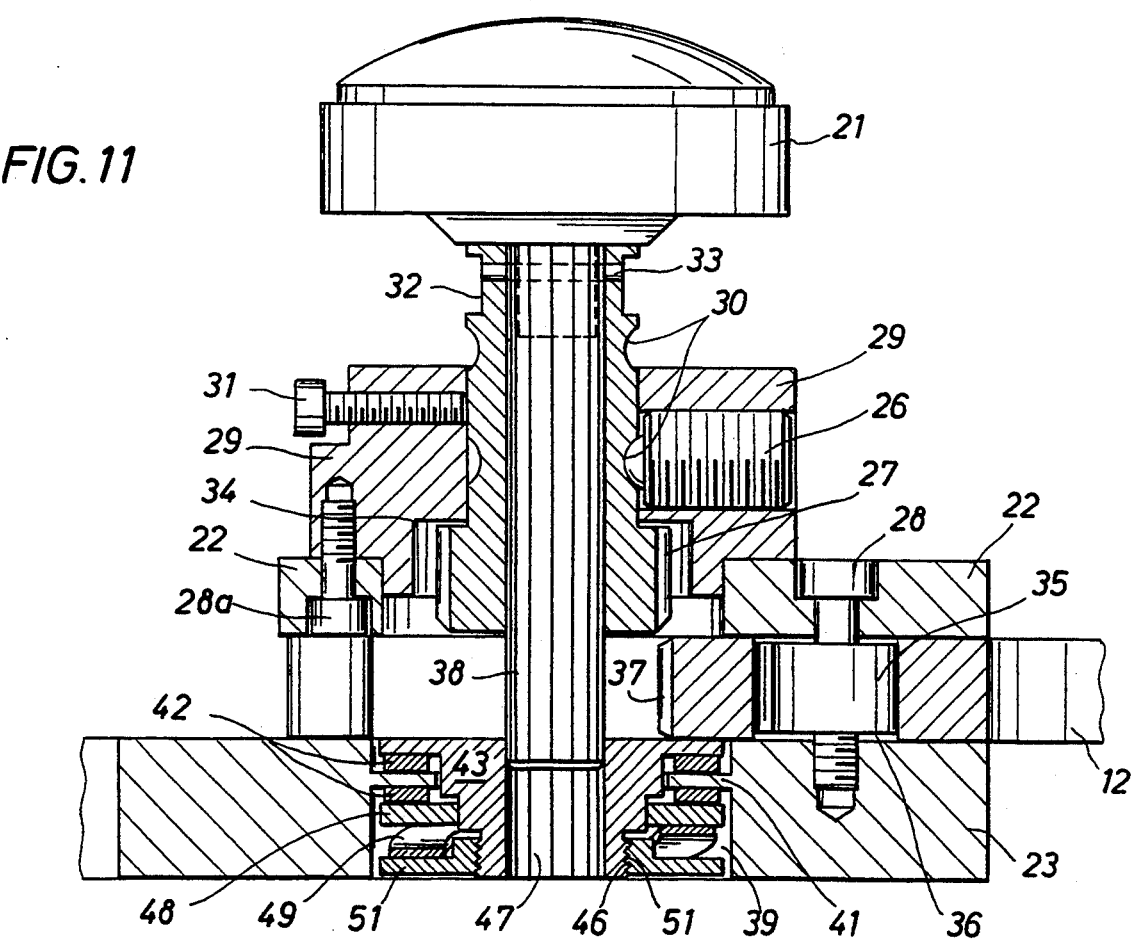
FIG. 11 is a sectional view of the arc mechanism showing the knob in the extended position.

The knob 21 may be moved between a retracted position (FIG. 10) and an extended position (FIG. 11). In the retracted position, spline gear teeth 27 engage arc gear teeth 37 such that movement of knob 21 will move arc gear member 12. In the extended position, spline gear teeth 27 do not engage arc gear teeth 37, and arc gear member 12 is free to slide in an arc shaped path as limited by upper plate 22, lower plate 23, and roller 35 located within slot 36. This feature would generally only be used preoperatively or intraoperatively to correctly position the arc gear member 12. In both the retracted and extended positions, shaft gear teeth 38 engage clutch mechanism 40.

The combination of collar 29, upper plate 22, lower plate 23, with these elements being held together by plate fasteners 28 and collar fasteners 28a, form the body of drive means 13.

Spline gear 24 is slideably mounted within collar 29. Upon being moved from the retracted position to the extended position, collar shoulder 34 limits movement in the extended position. Spline gear 24 has two detent grooves 30, the upper groove mating with detent screw 26 when in the retracted position and the lower groove mating with detent screw 26 when in the extended position. Detent screw 26 may be tightened to increase the force required to move the knob 21 to the extended position or loosened to decrease the force required.

Collar 29 is designed to accept safety screw 31, which, when tightened with knob 21 in the retracted position, mates with safety groove 32 in spline gear 24 to prevent movement towards the extended direction.

As previously mentioned, shaft gear teeth 38 engage clutch mechanism 40 which controls the force required to turn knob 21. The preferred embodiment of clutch mechanism 40 is shown in FIGS. 10 and 11. Clutch mechanism 40 is contained within lower plate 23 which has an open circular area 39, the center of which is located axially in line with gear shaft 25, with an extension section 41 into the circular area 39.

Shaft gear teeth 38 engage clutch body internal teeth 47 so as to turn clutch body 43. Clutch body 43 has several integral sections: clutch body plate 44, clutch body hex section 45, and clutch body threaded section 46.

Additional elements of clutch mechanism 40 are: two clutch plates 42, pressure plate 48, preload washer 49, and clutch nut 50. Clutch mechanism 40 is assembled by placing clutch body 43 and one clutch plate 42 within the open circular area 39 such that these elements rest on extension section 41. The second clutch plate 42, pressure plate 48, preload washer 49 and clutch nut 50 are stacked, the clutch nut threaded section 51 is threaded with the corresponding clutch body threaded section 46, and the clutch nut 50 is tightened to a predetermined torque. Here, pressure plate 48 is a plate shape member with an open hexagonal central area which mates with the clutch body hex section 45, such that pressure plate 48 turns with clutch body 43. Also, preload washer 49 is shaped as a "wavy washer."

The clutch mechanism 40 operates by causing friction between the elements in rotational movement (clutch body plate 44 and pressure plate 48, through clutch plates 42) and the stationary lower plate extension section 41. As more torque is applied to clutch nut 50, it becomes harder to turn knob 21.

Figure 13:
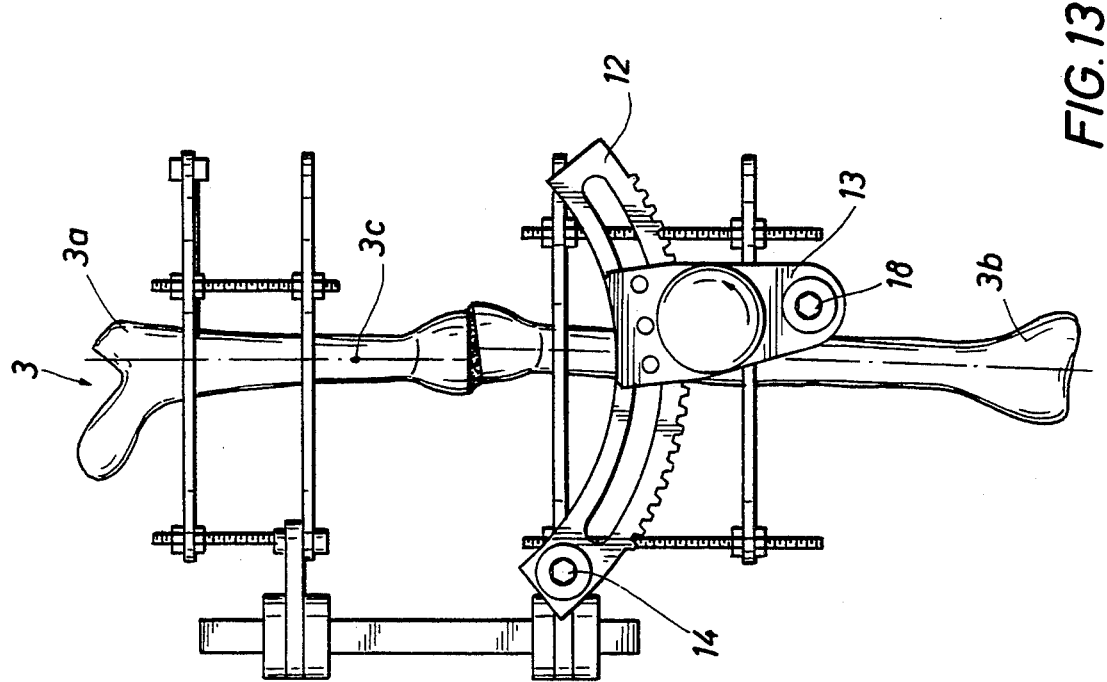
FIG. 13 is a view of the bone and device of FIG. 12 showing movement of the arc gear member to correct the deformity.
Figure 12:
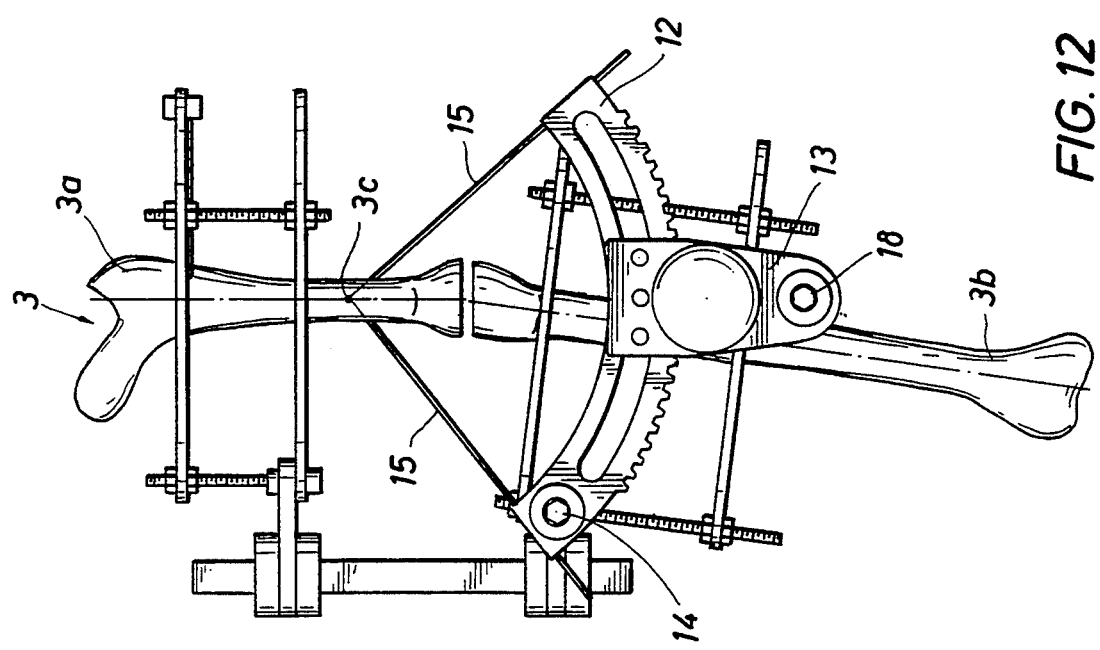
FIG. 12 is a view of a deformed bone wherein the focal point required to correct the deformity is located proximal to the area of the deformity.

FIG. 12 shows a bone 3 (shown in the plane of deformity) with a deformity which requires the lower bone segment 3b to be rotated counter-clockwise in the plane of deformity (angular movement in the plane of deformity) with simultaneous translational-lateral movement to the right, such that the axis of the lower bone segment 3b is in line with the axis of the upper bone segment 3a. This desired movement can be achieved by positioning the arc mechanism 10 such that focal point 3c is located proximal to the deformity bulge in bone 3, on the upper bone segment 3a. Movement of the lower bone segment 3b is shown in FIG. 13. As seen in FIG. 13, movement of the lower bone segment 3b through an arc shaped path with focal point 3c brings the axis of the lower bone segment 3b in line with the axis of the upper bone segment 3a. Here, as in FIGS. 3 and 4, the arc gear member 12 is located in a plane parallel to the plane of deformity and the intersection of alignment wires 15 is directly above the focal point 3c on bone 3 and in the same plane as arc gear member 12.

Figure 15:
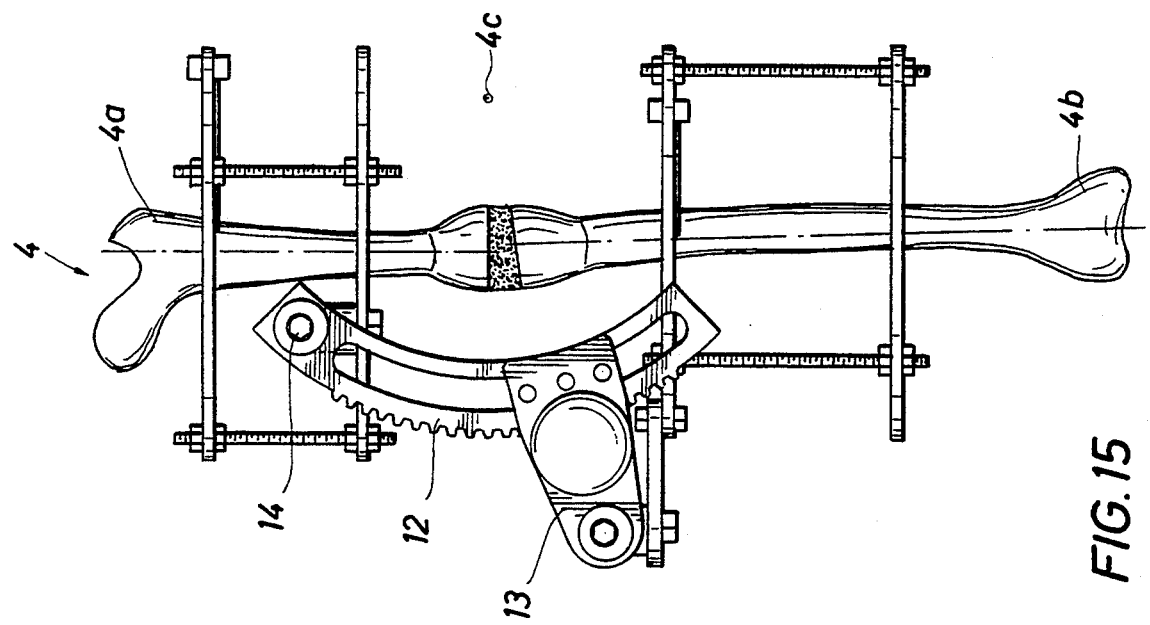
FIG. 15 is a view of the bone and device of FIG. 14 showing movement of the arc gear member to correct the deformity.
Figure 14:
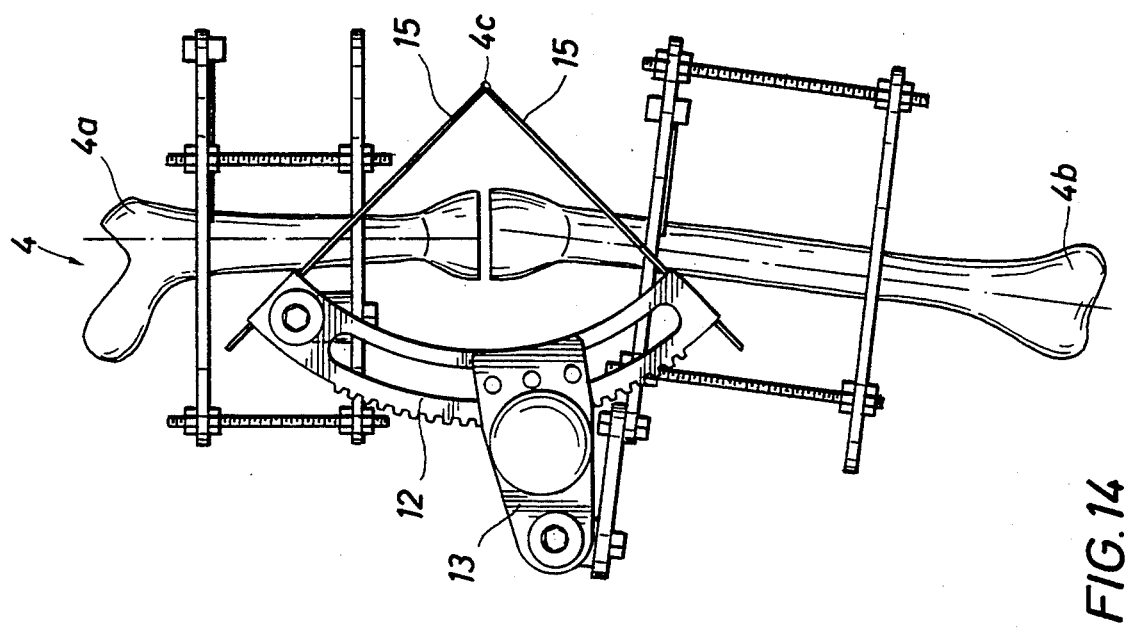
FIG. 14 is a view of a deformed bone wherein the focal point required to correct the deformity is located to the side of the area of the deformity.

FIG. 14 shows a bone 4 (shown in the plane of deformity) with a deformity which requires the lower bone segment 4b to be rotated counter-clockwise in the plane of deformity (angular movement) with simultaneous translational-extension movement (extending the overall length). This desired movement can be achieved by positioning the arc mechanism 10 such that focal point 4c is located to the right of bone 4 as shown in FIG. 14. As shown in FIG. 15, manipulation of drive means 13 causes movement of arc gear member 12 and corrects this deformity by simultaneous aligning the axes of the upper and lower bone segments 3a, 3b and extending the length of the bone.

FIG. 16 shows a bone 5 with a deformity which requires that one bone segment 5a, 5b be rotated about the axis of the bone 5. The proper placement of the arc mechanism 10 is shown in FIGS. 16–18. Here, the plane of deformity is any plane perpendicular to the axis of the bone 5. Thus, arc gear member 12 may be positioned in any plane perpendicular to the axis of bone 5. For purely rotational movement, the focal point 5c is located at the axis of the bone 5. The operation of the arc mechanism 10 shown in FIGS. 16–18 would cause clockwise rotation of bone segment 5b.

Figure 20:
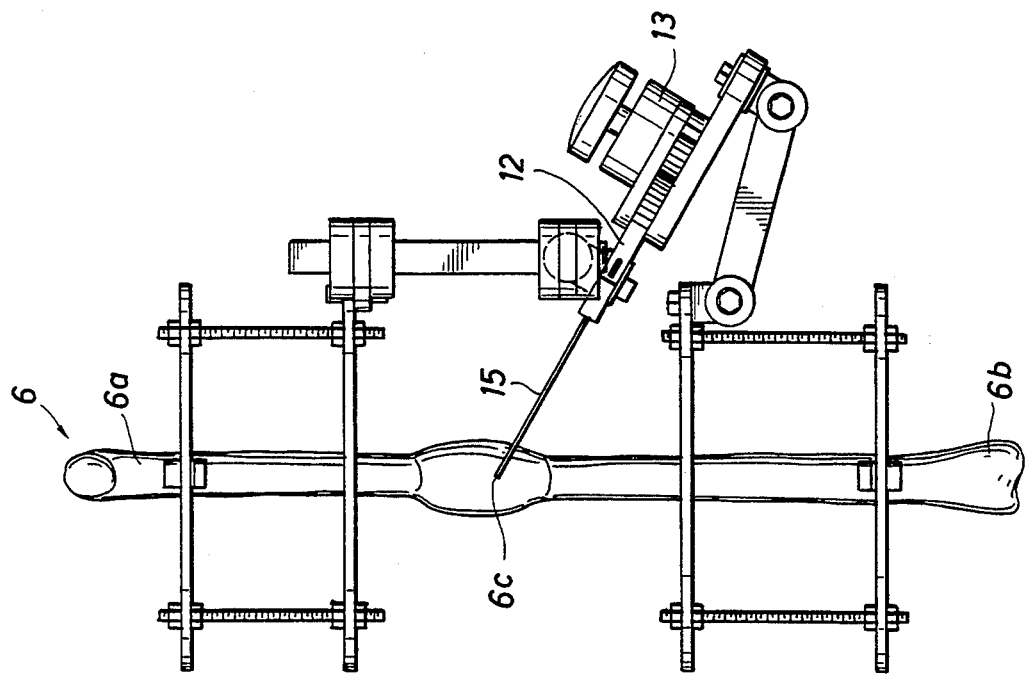
FIG. 20 is a side view taken in the direction indicated by lines 20—20 of FIG. 19.
Figure 19:
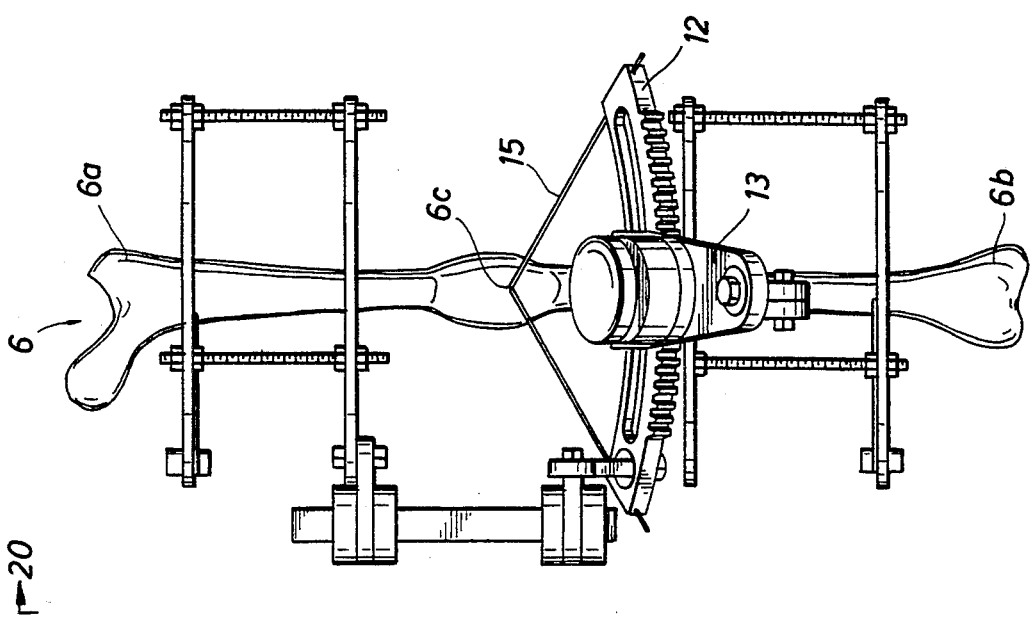
FIG. 19 is a view of the device attached to a bone which has undergone correction which required both rotational movement and angular movement.

FIGS. 19–20 show a bone 6 which has been straightened to correct a deformity which required both an angular and a rotational movement. The placement of the arc gear member 12 in a plane which slants as shown relative to the bone 6 imparts both a rotational component and an angular component. Here, the plane of deformity is that plane in which arc gear member 12 and alignment wires 15 are located. The focal point 6c is that point at which alignment wires 15 intersect.

The above corrections of deformities are illustrative of the movements and corrections which can be achieved with the device 1. Generally, this device 1 may be used whenever a rotational movement or arc shaped movement may be used to correct the deformity. The design of the device 1 and the flexibility provided by support braces 11a, 11b allow the arc mechanism 10 to be placed in virtually any plane and located with virtually any focal point. The device 1 may be used to correct a vast variety of deformities ranging from those requiring simple rotational or angular movement to those requiring complex movement with components of angular, rotational and translational movement.

Figure 21:
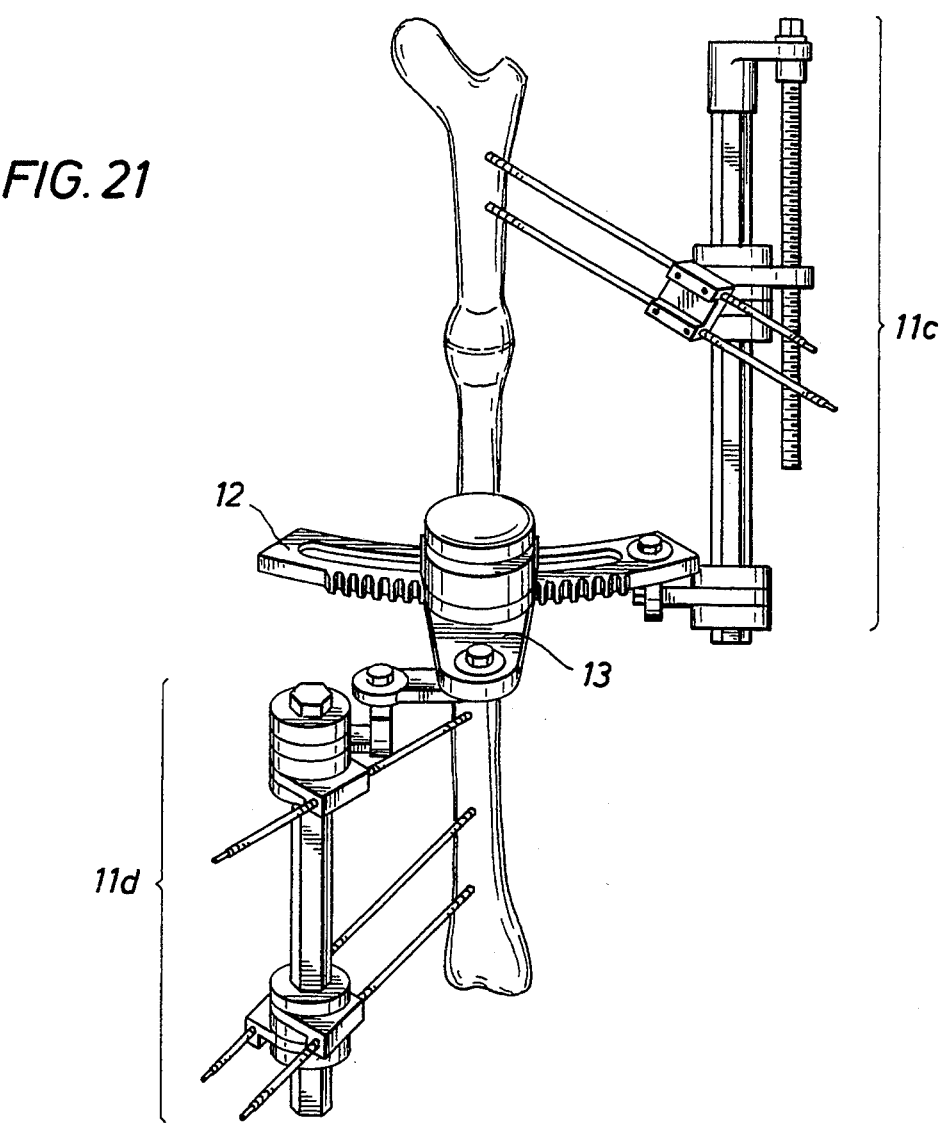
FIG. 21 shows an alternate embodiment of the support braces.

FIG. 21 shows the bone 6 of FIGS. 19–20 with an alternate embodiment of support braces 11c, 11d. Support braces 11a, 11b 11c, 11a may be any type of external brace. Generally, there are two types of external braces; circular, as represented by support braces 11a (generally referred to as the "Ilizarov System"), or lateral, as represented by support braces 11b11c, 11d. (The lateral model depicted is the HEX-FIX TM, marketed by Smith & Nephew Richards, Inc.) Generally, circular support braces 11a function by extending a wire through the skin, soft tissue and bone, through both sides of the body part. The extending ends of the wire are secured to a circular member at approximately the diameter of the circular member. Often, two or more circular members are combined to form a cylindrically shaped support brace 11a, each circular member having a wire extending across the diameter of the circular member which passes through the bone. Lateral support braces 11b, 11c, 11d generally consist of a rod and means to attach the rod to a pin which is inserted through the skin and into the bone. Lateral support systems may include peripheral equipment such as ball joints, universal joints, and pivotal connection members.

The selection of a particular type or model of external brace is immaterial to the inventive device 1 and relies heavily on an individual surgeon's preference. Thus, a surgeon may choose from many type, models, and manufacturers of external braces or combinations thereof. However, it is important in the selection of an external brace that the brace allow the correct placement of the arc mechanism 10 and allow secure attachment at attachment point 14 and drive attachment point 18. It is intended that any make or model of external brace meeting these requirements fall within the scope of the appended claims.

Figure 23:
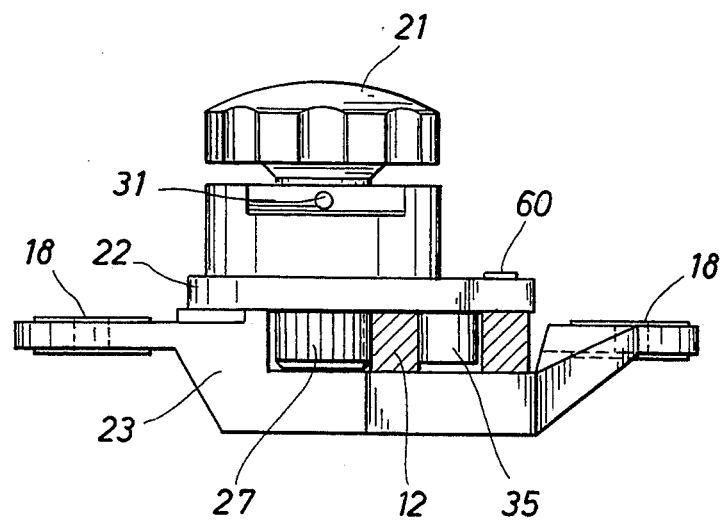
FIG. 23 is a side view taken in the direction indicated by lines 23—23 of FIG. 22.

FIGS. 22–23 show an embodiment of the arc mechanism 10 having the additional features of an additional attachment point 14, an additional drive attachment point 18, a thumb switch 60, arc gear member holes 70, and a scale 71. The additional attachment points 14, 18 provide additional flexibility to secure the arc mechanism 10 to various external braces. Thumb switch 60, arc gear member holes 70 and scale 71, as discussed below, provide means to measure and control the amount of movement.

FIGS. 24–25 show the operation of thumb switch 60. Thumb switch 60, leaf spring 61 and pin 62 cooperate as shown to selectively prevent movement of arc gear member 12 relative to drive means 13. As shown, these components are located within a hollowed section of upper plate 22 (FIG. 10), directly above the arc gear member holes 70. FIG. 24 shows the thumb switch 60 and pin 62 in the engaged position with the pin 62 extending through lower hole 63 and engaging the arc gear member 12 via holes 70. FIG. 25 shows the thumb switch 60 and pin 62 in the disengaged position, allowing arc gear member 12 to slide relative to drive means 13. Leaf spring 61 serves to bias pin 62 towards the downward, engaged position and bias thumb switch to the left as shown. To disengage, thumb switch 60 is pushed to the right, thereby lifting leaf spring 61 and pin 62, the central portion of pin 62 being engaged with leaf spring 61. When disengaged, preferably pin 62 projects through upper hole 64, thereby giving the patient and/or medical personnel a visual indication that the thumb switch 60 and pin 62 is disengaged. Preferably, arc gear member holes 70 correspond with scale 71, e.g. the holes 70 being located at 1° degree increments.

With the present device 1, it is desirable for the surgeon and patient to be able to measure and control the amount of movement. The desired movement rate varies with the individual patient based on factors such as age and general health. If movement occurs too fast, the bone doesn't set properly. If movement occurs too slow, the bone may set prematurely. Movement measurement and control may be achieved by providing markings on arc member 12, e.g., the degree markings of scale 71, or by providing appropriate markings on knob 21 and/or the body of drive means 13 (markings not shown).

The fixation brace with focal hinge device 1 solves the problems mentioned above by providing a compact, non-obstructive external fixation device with an integral drive mechanism which is capable of moving two bone segments relative to each other through a vast range of corrective movements while allowing easy, accurate alignment and placement of the device.

Having described the invention above, various modifications of the techniques, procedures, material and equipment will be apparent to those skilled in the art. It is intended that all such variations within the scope and spirit of the invention be included within the scope of the appended claims.

We claim:

1. A device for moving a first bone segment relative to a second bone segment to externally fix bone fractures and to correct bone deformities, the first and second bone segments having a plane of deformity and a focal point, comprising:
    an arc mechanism having an arc gear member having radii and an attachment point, and a drive means for moving the arc gear member relative to the drive means such that the attachment point moves through an arc shaped path in the plane of the arc gear member;
    a first attachment means to secure the attachment point of the arc gear member to the first bone segment;
    a second attachment means to secure the drive means to the second bone segment;
    means for aligning and positioning the device in a plane for moving the first bone segment, at the attachment point, in an arc shaped path, such that the device will move the first bone segment into a predetermined position in relation to the second bone segment;
    wherein the first and second attachment means are designed to allow the arc gear member to selectively be placed about the first and second bone segments so as to allow the arc gear member to be placed in the plane of deformity with the radii intersecting at the focal point.

2. The device of claim 1, wherein the arc gear member comprises an arc shaped track of gear teeth.

3. The device of claim 2, wherein the drive means comprises a rotatable gear which engages the arc shaped track of gear teeth on the arc gear member, which, upon rotation moves the arc gear member through an arc shaped path.

4. The device of claim 3, wherein the means for aligning and positioning the device comprises at least two wires, each removably attached to the arc gear member and extending in a radial direction.

5. The device of claim 4, wherein at least one of the first and second attachment means comprises a circular support brace having at least two circular members, wherein each circular member is designed to secure a wire extended across the diameter of the circular member and passed through the bone segment.

6. The device of claim 4, wherein at least one of the first and second attachment means comprises a lateral support brace comprising a rod and a multiplicity of pins designed to be secured to the bone segment and to the rod.

7. The device of claim 2, wherein the arc gear member is arc shaped.

8. The device of claim 7, wherein the sector of the arc gear member is between about 10° and about 90°.

9. The device of claim 7, wherein the arc gear member has an arc shaped slot.

10. The device of claim 9, wherein the drive means comprises a multiplicity of rollers designed to extend into the arc shaped slot and to interface with the arc gear member to prevent radial movement.

11. The device of claim 3, wherein the drive means comprises means for extending the rotatable gear away from engagement with the arc shaped track of gear teeth so as to allow the arc gear member to slide in a predetermined path.

12. The device of claim 11, wherein the drive means comprises a means to selectively limit movement of the rotatable gear from a retracted position to the extended position.

13. The device of claim 3, wherein the drive means comprises a clutch means for adjustably controlling the amount of force required to rotate the rotatable gear.

14. The device of claim 3, further comprising means to measure movement of the arc gear member relative to the drive means.

15. The device of claim 3, further comprising means to selectively prevent movement of the arc gear member relative to the drive means.

16. A device for moving a first bone segment relative to a second bone segment to externally fix bone fractures and to correct bone deformities, comprising:
    an arc shaped arc gear member having an arc shaped track of gear teeth;
    a drive means having a rotatable gear which engages the arc shaped track of gear teeth on the arc gear member and means to slidably engage the arc gear member such that the arc gear member can slide in an arc shaped path;
    means for detachably engaging at least two alignment wires to the arc gear member such that the alignment wires extend in the radial direction;
    a first attachment means to secure the arc gear member to the first bone segment;
    a second attachment means to secure the drive means to the second bone segment.

17. The device of claim 16, wherein at least one of the first and second attachment means comprises a circular support brace having at least two circular members, wherein each circular member is designed to secure a wire extended across the diameter of the circular member and passed through the bone segment.

18. The device of claim 16, wherein at least one of the first and second attachment means comprises a lateral support brace comprising a rod and a multiplicity of pins designed to be secured to the bone segment and to the rod.

19. The device of claim 16, wherein the sector of the arc gear member is between about 10° and about 90°.

20. The device of claim 16, wherein the arc gear member has an arc shaped slot.

21. The device of claim 20, wherein the means to slidably engage the arc gear member comprises a multiplicity of rollers designed to extend into the arc shaped slot and to interface with the arc gear member to prevent radial movement.

22. The device of claim 16, further comprising means for extending the rotatable gear away from engagement with the arc shaped track of gear teeth so as to allow the arc gear member to slide in an arc shaped path.

23. The device of claim 22, further comprising means to selectively limit movement of the rotatable gear from a retracted position to the extended position.

24. The device of claim 16, further comprising clutch means for adjustably controlling the amount of force required to rotate the rotatable gear.

25. The device of claim 16, further comprising means to measure movement of the arc gear member relative to the drive means.

26. The device of claim 16, further comprising means to selectively prevent movement of the arc gear member relative to the drive means.

27. A method for moving a first bone segment relative to a second bone segment to externally fix bone fractures and to correct bone deformities, comprising the steps of:
   obtaining an arc mechanism having an arc gear member and drive means, the arc gear member having radii;
   determining a plane of deformity and a focal point required to correct the bone deformity;
   positioning the arc gear member in the plane of deformity such that the radii intersect at the focal point required to correct the deformity;
   securing the arc gear member to the first bone segment;
   securing the drive means to the second bone segment;
   manipulating the drive means to move the arc gear member such that the first bone segment is moved through an arc shaped range of motion relative to the second bone segment.

28. The method of claim 27, wherein the arc gear member comprises an arc shaped track of gear teeth.

29. The method of claim 28, wherein the drive means comprises a rotatable gear which engages the arc shaped track of gear teeth, such that, upon rotation, the arc gear member moves in an arc shaped path relative to the drive means.

30. The method of claim 29, wherein securing the arc gear member to the first bone segment comprises the steps of:
   inserting a first wire through the first bone segment;
   extending the first wire across the diameter of a first circular member;
   inserting a second wire through the first bone segment;
   extending the second wire across the diameter of a second circular member;
   connecting the first circular member to the second circular member;
   attaching the arc gear member to the connected first and second circular members.

31. The method of claim 29, wherein securing the drive means to the second bone segment comprises the steps of:
   inserting a first wire through the second bone segment;
   extending the first wire across the diameter of a first circular member;
   inserting a second wire through the second bone segment;
   extending the second wire across the diameter of a second circular member:
   connecting the first circular member to the second circular member;
   attaching the drive means to the connected first and second circular members.

32. The method of claim 29, wherein securing the arc gear member to the first bone segment comprises the steps of:
   inserting a multiplicity of pins into the first bone segment;
   locating a rod lateral to the first bone segment;
   connecting the pins to the rod;
   attaching the arc gear member to the rod.

33. The method of claim 29, wherein securing the drive means to the second bone segment comprises the steps of:
   inserting a multiplicity of pins into the second bone segment;
   locating a rod lateral to the second bone segment;
   connecting the pins to the rod;
   attaching the arc gear member to the rod.

* * * * *